United States Patent
Zhao et al.

(10) Patent No.: US 10,162,068 B1
(45) Date of Patent: Dec. 25, 2018

(54) CALIBRATING TIME IN PET DEVICE (71) Applicant: Shenyang Neusoft Medical Systems Co., Ltd., Shenyang (CN)

(72) Inventors: Jian Zhao, Shenyang (CN); Guocheng Wu, Shenyang (CN); Xi Wang, Shenyang (CN); Baowei Xu, Shenyang (CN); Guodong Liang, Shenyang (CN); Nan Li, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 0 days.

(21) Appl. No.: 16/019,103

(22) Filed: Jun. 26, 2018

(30) Foreign Application Priority Data

Jun. 26, 2017 (CN) .......................... 2017 1 0493862

(51) Int. Cl.
*G01T 1/29* (2006.01)
*A61B 6/03* (2006.01)
*G01T 7/00* (2006.01)
*A61B 6/00* (2006.01)
*G01R 33/48* (2006.01)

(52) U.S. Cl.
CPC ............ *G01T 1/2985* (2013.01); *A61B 6/037* (2013.01); *A61B 6/5288* (2013.01); *A61B 6/582* (2013.01); *G01T 7/005* (2013.01); *G01R 33/4808* (2013.01)

(58) Field of Classification Search
CPC ....... A61B 6/037; A61B 6/5288; A61B 6/582; G01R 33/4808; G01T 1/2985; G01T 7/005
See application file for complete search history.

(56) References Cited

U.S. PATENT DOCUMENTS

| 8,796,637 B1 | 8/2014 | Burr et al. | |
|---|---|---|---|
| 2003/0047686 A1* | 3/2003 | Fries | G01T 1/2985 250/363.03 |
| 2004/0195512 A1* | 10/2004 | Crosetto | A61B 6/037 250/363.04 |

(Continued)

FOREIGN PATENT DOCUMENTS

| CN | 103488247 A | 1/2014 |
|---|---|---|
| CN | 103961126 A | 8/2014 |

(Continued)

OTHER PUBLICATIONS

State Intellectual Property Office of the People's Republic of China, Office Action and Search Report Issued in Application No. 201710493862.6, dated Oct. 29, 2018, 4 pages, (Submitted with Machine Translation).

(Continued)

*Primary Examiner* — Mark R Gaworecki
(74) *Attorney, Agent, or Firm* — Fish & Richardson P.C.

(57) ABSTRACT

A method of calibrating time in a Positron Emission Computed Tomography (PET) device includes determining a rising edge slope of an electrical signal corresponding to a photon which is detected by a detector of the PET device when the PET device is used to scan a part of a subject to be examined. The method includes determining a time shift corresponding to the rising edge slope based on a correspondence between the rising edge slope and the time shift; calibrating time information of the photon based on the time shift; and reconstructing a PET image of the part of the subject to be examined based on the calibrated time information of the photon.

20 Claims, 4 Drawing Sheets (56) References Cited

U.S. PATENT DOCUMENTS

| | | | |
|---|---|---|---|
| 2005/0247879 A1* | 11/2005 | Xie | G01T 1/2985 |
| | | | 250/363.03 |
| 2010/0078569 A1 | 4/2010 | Jarron et al. | |
| 2011/0210255 A1 | 9/2011 | Kim et al. | |
| 2015/0285922 A1 | 10/2015 | Mintzer et al. | |
| 2016/0084974 A1* | 3/2016 | Lerche | G01T 1/1642 |
| | | | 250/362 |
| 2016/0291175 A1* | 10/2016 | Deng | G01T 1/2985 |
| 2016/0299240 A1 | 10/2016 | Cho et al. | |
| 2017/0302281 A1* | 10/2017 | Ning | G01T 1/2985 |

FOREIGN PATENT DOCUMENTS

| | | |
|---|---|---|
| CN | 103969675 A | 8/2014 |
| CN | 105193442 A | 12/2015 |
| CN | 105737853 A | 7/2016 |
| CN | 106716179 A | 5/2017 |

OTHER PUBLICATIONS

European Patent Office, Extended European Search Report Issued in Application No. 18182480.6, dated Oct. 22, 2018, Germany, 10 pages.
Schug David et al: "Crystal Delay and Time Walk Correction Methods for Coincidence Resolving Time Improvements of a Digtal-Silicon-Photomultiplier- Based PET/MRI Insert". IEEE Transactions On Radiation And Plasma Medical Sciences, IEEE. vol. 1, No. 2, Mar. 1, 2017(Mar. 1, 2017), pp. 178-190, XP011643930, ISSN: 2469-7311, DOI: 10.1109/TNS.2017.2654920 [retrieved on Mar. 24, 2017] p. 179-p. 189.

* cited by examiner

CALIBRATING TIME IN PET DEVICE

CROSS REFERENCE TO RELATED APPLICATIONS

This application claims priority to Chinese Patent Application No. 201710493862.6, filed on Jun. 26, 2017, the entire content of which is incorporated herein by reference.

BACKGROUND

In a Positron Emission Computed Tomography (PET) device, an isotope-labeled drug (such as an imaging agent) having positron emission capability is injected into a subject. The isotope-labeled drug may be, for instance, one or more of a carbon isotope, a fluorine isotope, an oxygen isotope, and a nitrogen isotope. The isotope-labeled drug may participate in a physiological metabolism of the subject and an annihilation event can occur during the physiological metabolism.

Figures 1, 2:
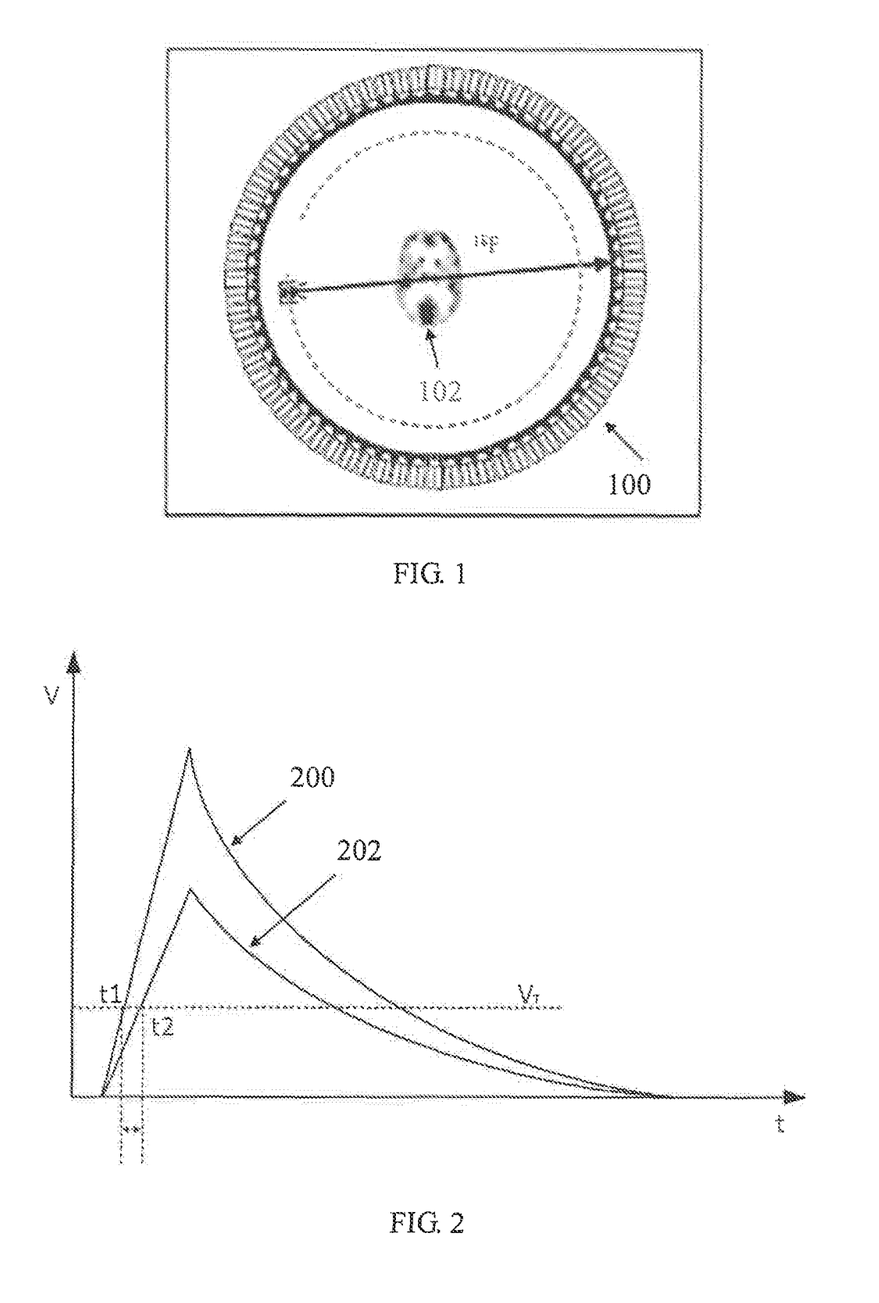
FIG. 1 is a schematic diagram of a PET detector.
FIG. 2 is a plot of a time shift.

FIG. 1 is a schematic diagram of an example PET detector 100. An annihilation event in a subject 102 generates two gamma photons each having an energy of approximately 0.511 MeV and moving in opposite directions.

Since an ability of respective parts of the subject to absorb the isotope-labeled drug can differ, a concentration of the isotope in the respective parts of the subject can be different and an intensity of respective gamma photons generated by annihilation events can also be different. The PET detector 100 surrounding the subject 102 may detect time information, position information, energy information and direction information of a photon from an annihilation event. The photon signal can be converted into an electrical signal such as current or voltage by a photoelectric converter. An electronic acquisition system and a computer system may perform tasks including one or more of acquisition, analog/digital conversion, storage, calculation, and image reconstruction for the electrical signal to obtain images of the subject, such as one or more of cross-sectional, coronal, and sagittal images of organs of the subject. Tissues or lesions with a high metabolic rate exhibit relatively bright signals on a PET reconstructed image, and tissues or lesions with a low metabolic rate exhibit relatively dark signals on the PET reconstructed image.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure relates to calibrating time in a Positron Emission Computed Tomography (PET) device.

In an aspect, a method of calibrating time in a Positron Emission Computed Tomography (PET) device includes determining a rising edge slope of an electrical signal corresponding to a photon which is detected by a detector of the PET device when the PET device is used to scan a part of a subject to be examined. The method includes determining a time shift corresponding to the rising edge slope based on a correspondence between the rising edge slope and the time shift; calibrating time information of the photon based on the time shift; and reconstructing a PET image of the part of the subject to be examined based on the calibrated time information of the photon.

Embodiments can include one or more of the following features.

Determining the rising edge slope of the electrical signal includes obtaining a first amplitude at a first moment and a second amplitude at a second moment in a rising edge process of the electrical signal; determining an amplitude difference between the first amplitude and the second amplitude; determining a time difference between the first moment and the second moment; and determining a ratio between the amplitude difference and the time difference, the ratio being taken as the rising edge slope. Obtaining the first amplitude at the first moment and the second amplitude at the second moment in the rising edge process of the electrical signal includes receiving the electrical signal at a first input of a first comparator and a first input of a second comparator; receiving a first threshold at a second input of the first comparator, the first amplitude being equal to the first threshold; receiving a second threshold at a second input of the second comparator, the second amplitude being equal to the second threshold, and the second threshold being greater than the first threshold; recording an inverting time of the first comparator as the first moment; and recording an inverting time of the second comparator as the second moment. Obtaining the first amplitude at the first moment and the second amplitude at the second moment in the rising edge process of the electrical signal includes receiving the electrical signal at a first input of a third comparator and an input of an analog-to-digital converter; receiving a third threshold at a second input of the third comparator, wherein an output of the third comparator is coupled to a control input of the analog-to-digital converter such that an inversion of the third comparator triggers the analog-to-digital converter to perform a sample for an amplitude of the electrical signal, and wherein the time difference is equal to a sampling period of the analog-to-digital converter; and obtaining two sampling values from successive samplings of the electrical signal by the analog-to-digital converter, the two sampling values being the first and second amplitudes.

The method includes obtaining the correspondence between the rising edge slope and the time shift for the PET device prior to the PET device being used to scan the part of the subject to be examined. Obtaining the correspondence between rising edge slope and time shift includes determining a rising edge slope of a test electrical signal corresponding to a test photon from a test source detected by the detector of the PET device when the PET device performs a system calibration process; obtaining a time shift of the test photon based on time information of the test photon and time information of a standard photon from a standard source; and obtaining the correspondence by fitting based on time shifts and rising edge slopes of test electrical signals corresponding to at least two test photons. Determining the rising edge slope of the test electrical signal includes obtaining a first amplitude at a first moment and a second amplitude at a second moment in a rising edge process of the test electrical signal; determining an amplitude difference between the first amplitude and the second amplitude; determining a time difference between the first moment and the second moment; and determining a ratio between the amplitude difference and the time difference, the ratio being taken as the rising edge slope. Obtaining the first amplitude at the first moment and the second amplitude at the second moment in the rising edge process of the test electrical signal includes receiving the test electrical signal at a first input of a first comparator and a first input of a second comparator; receiving a first threshold at a second input of the first comparator, the first amplitude being equal to the first threshold, receiving a second threshold at a second input of the second comparator, the second amplitude being equal to the second threshold, the second threshold being greater than the first threshold; recording an inverting time of the first comparator as the first moment; and recording an inverting time of the second comparator as the second moment. Obtaining the first amplitude at the first moment and the second amplitude at the second moment in the rising edge process of the test electrical signal includes receiving the test electrical signal at a first input of a third comparator and an input of an analog-to-digital converter; receiving a third threshold at a second input of the third comparator, wherein an output of the third comparator is coupled to a control input of the analog-to-digital converter such that an inversion of the third comparator triggers the analog-to-digital converter to perform a sample for an amplitude of the test electrical signal; wherein the time difference is equal to a sampling period of the analog-to-digital converter; obtaining two sampling values from successive sampling of the test electrical signal by the analog-to-digital converter, the two sampling values being the first and second amplitudes. Determining the rising edge slope of the test electrical signal includes receiving the test electrical signal at a first input of a third comparator and an input of an analog-to-digital converter; receiving a third threshold at a second input of the third comparator, wherein an output of the third comparator is coupled to a control input of the analog-to-digital converter such that an inversion of the third comparator triggers the analog-to-digital converter to perform a sample for an amplitude of the test electrical signal; obtaining at least three sampling values from successive sampling of the test electrical signal by the analog-to-digital converter; and determining the rising edge slope of the test electrical signal based on the at least three sampling values and the sampling period of the analog-to-digital converter.

In an aspect, a PET device includes a detector; one or more processors; and a non-transitory machine readable storage medium. The one or more processors are configured to invoke machine executable instructions stored on the non-transitory machine readable storage medium to determine a rising edge slope of an electrical signal corresponding to a photon which is detected by the detector when the PET device is used to scan a part of a subject to be examined; determine a time shift corresponding to the rising edge slope based on a correspondence between the rising edge slope and the time shift; calibrating time information of the photon based on the time shift; and reconstruct a PET image of the part of the subject to be examined based on the calibrated time information of the photon.

Embodiments can include one or more of the following features.

Determining the rising edge slope of the electrical signal includes obtaining a first amplitude at a first moment and a second amplitude at a second moment in a rising edge process of the electrical signal; determining an amplitude difference between the first amplitude and the second amplitude; determining a time difference between the first moment and the second moment; and determining a ratio between the amplitude difference and the time difference, the ratio being taken as the rising edge slope.

The device includes a first comparator and a second comparator. Obtaining the first amplitude at the first moment and the second amplitude at the second moment in the rising edge process of the electrical signal includes receiving the electrical signal at a first input of the first comparator and a first input of the second comparator; receiving a first threshold at a second input of the first comparator, the first amplitude being equal to the first threshold, receiving a second threshold at a second input of the second comparator, the second amplitude being equal to the second threshold, and the second threshold being greater than the first threshold; recording an inverting time of the first comparator as the first moment; and recording an inverting time of the second comparator as the second moment.

The device includes a third comparator and an analog-to-digital converter. Obtaining the first amplitude at the first moment and the second amplitude at the second moment in the rising edge process of the electrical signal includes receiving the electrical signal at a first input of the third comparator and an input of the analog-to-digital converter; receiving a third threshold at a second input of the third comparator, wherein an output of the third comparator is coupled to a control input of the analog-to-digital converter such that an inversion of the third comparator triggers the analog-to-digital converter to perform a sample for an amplitude of the electrical signal, and wherein the time difference is equal to a sampling period of the analog-to-digital converter; and obtaining two sampling values from successive samplings of the electrical signal by the analog-to-digital converter, the two sampling values being the first and second amplitudes.

The one or more processors are configured to invoke the machine executable instructions to obtain the correspondence between the rising edge slope and the time shift for the PET device prior to the PET device being used to scan the part of the subject to be examined. Obtaining the correspondence between rising edge slope and time shift includes determining a rising edge slope of a test electrical signal corresponding to a test photon from a test source detected by the detector of the PET device when the PET device performs a system calibration process; obtaining a time shift of the test photon based on time information of the test photon and time information of a standard photon from a standard source; and obtaining the correspondence by fitting based on time shifts and rising edge slopes of test electrical signals corresponding to at least two test photons. Determining the rising edge slope of the test electrical signal includes obtaining a first amplitude at a first moment and a second amplitude at a second moment in a rising edge process of the test electrical signal; determining an amplitude difference between the first amplitude and the second amplitude; determining a time difference between the first moment and the second moment; and determining a ratio between the amplitude difference and the time difference, the ratio being taken as the rising edge slope. The device includes a first comparator and a second comparator. Obtaining the first amplitude at the first moment and the second amplitude at the second moment in the rising edge process of the test electrical signal includes receiving the test electrical signal at a first input of the first comparator and a first input of the second comparator; receiving a first threshold at a second input of the first comparator, the first amplitude being equal to the first threshold, receiving a second threshold at a second input of the second comparator, the second amplitude being equal to the second threshold, and the second threshold being greater than the first threshold; recording an inverting time of the first comparator as the first moment; and recording an inverting time of the second comparator as the second moment. The device includes a third comparator and an analog-to-digital converter. Obtaining the first amplitude at the first moment and the second amplitude at the second moment in the rising edge process of the test electrical signal includes receiving the test electrical signal at a first input of the third comparator and an input of the analog-to-digital converter; receiving a third threshold at a second input of the third comparator, wherein an output of the third comparator is coupled to a control input of the analog-to-digital converter such that an inversion of the third comparator triggers the analog-to-digital converter to perform a sample for an amplitude of the test electrical signal, and wherein the time difference is equal to a sampling period of the analog-to-digital converter; and obtaining two sampling values from successive samplings of the test electrical signal by the analog-to-digital converter, the two sampling values being the first and second amplitudes.

The processor includes one or more of a Field-Programmable Gate Array (FPGA) or a Time-to-Digital Converter (TDC).

The approaches to calibrating time in a PET device described here can have one or more advantages, e.g., related to the improvement of the quality and accuracy of a reconstructed PET image. The collection of information of gamma photons may affect quality of a reconstructed PET image. Calibration of time information can enhance the accuracy of information of gamma photons, such as time and energy information, which in turn can contribute to improvements in the quality of the reconstructed PET images, e.g., PET images. Higher quality PET images can have advantages in improvements to diagnostics and treatment of patients.

DETAILED DESCRIPTION

We describe here an approach to calibrating time information in a PET device. PET devices record information about photon signals from annihilation events in an imaged subject. The shapes of pulse signals corresponding to photons with different energies are different, which means that there is a difference in the time information of photons of different energies. This disclosure relates generally to an approach to calibrating time information of a photon based on the rising edge slope of a pulse signal corresponding to the photon. The calibration of time information of a photon can improve accuracy and quality of reconstructed PET images, which can contribute to improved diagnostic and treatment outcomes for patients.

In an example, a single comparator is used to identify an over-threshold moment of an electrical signal corresponding to a photon (sometimes also referred to as time information of the photon). The over-threshold moment of the electrical signal indicates a moment at which an amplitude of the electrical signal begins to be greater than a threshold. Electrical signals corresponding to photons with different energies have different rising edge characteristics. There is a time difference between moments of photons with different energies identified by the comparator using a same threshold. This time difference is referred to as a time shift.

FIG. 2 is a schematic diagram of an example time shift. $V_T$ represents a threshold voltage of the comparator, a horizontal axis represents time, and a vertical axis represents a voltage value of an electrical signal corresponding to a photon detected by the detector (sometimes also referred to as the electrical signal corresponding to the photon or a pulse signal corresponding to the photon). FIG. 2 shows that for two electrical signals 200, 202 corresponding to two photons with different rising edge slopes, the two moments at which the voltages of the electrical signals 200, 202 pass the threshold voltage are $t_1$ and $t_2$, respectively. The time difference between $t_1$ and $t_2$ is the time shift due to the different photon energies.

Because the shapes of pulse signals corresponding to photons with different energies are different, there is a difference between time information of the photons of different energies obtained based on the over-threshold moments of the pulse signals. This disclosure relates generally to an approach to calibrating time information of a photon with a rising edge slope of a pulse signal corresponding to the photon. The calibration of time information of a photon can improve accuracy and quality of reconstructed PET images, which can contribute to improved diagnostic and treatment outcomes for patients.

Figure 3:
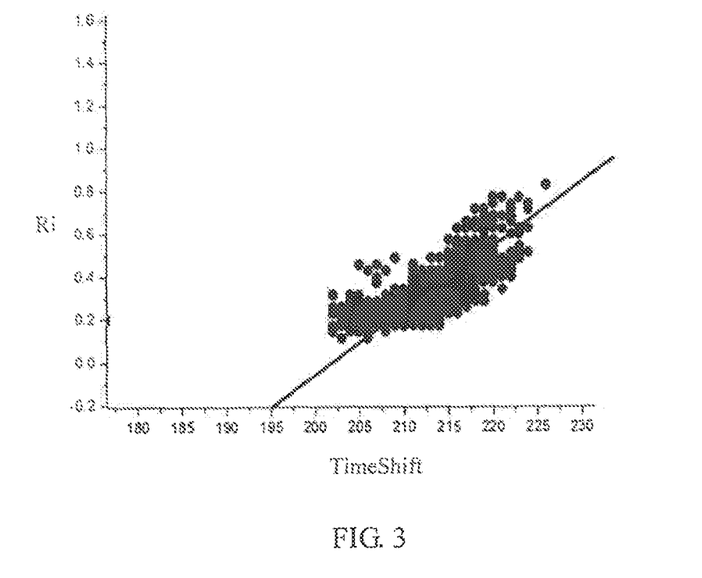
FIG. 3 is a plot of a correspondence between time shift and rising edge slope of an electrical signal corresponding to a photon.

In the approach to calibration of time information described here, a relationship between a rising edge slope of an electrical signal corresponding to a photon (referred to as the rising edge slope) and a time shift generated when time information of the photon is identified based on the electrical signal corresponding to the photon (referred to as the time shift) is obtained. FIG. 3 is a schematic diagram of an example correspondence between time shift (on the horizontal axis) and rising edge slope (on the vertical axis). In FIG. 3, the correspondence between time shift and rising edge slope was determined based on multiple tests.

As can be seen from FIG. 3, the correspondence between time shift and rising edge slope may be approximated as a linear relationship. In other words, the time shift may be roughly expressed as a linear function of the rising edge slope. In the context of this disclosure, the linear relationship between time shift and rising edge slope is used as an example. It can be understood that the correspondence may also be a nonlinear relationship.

When the correspondence between time shift and rising edge slope is a linear relationship, the linear relationship can be expressed as formula (1):

$$\text{TimeShift} = K * Ri + b \qquad (1).$$

Timeshift represents the time shift, K and b represent parameters, and $R_t$ represents the rising edge slope. The parameters K and b may be either decimal or integer values.

The time shift of a photon represents a difference between a theory moment at which the detector detects the photon and an over-threshold moment of the electrical signal of the photon. Thus, the time shift can be represented by formula (2):

$$\text{TimeShift} = T_z - T_s \qquad (2).$$

$T_Z$ represents the theory moment at which the detector detects a photon (sometimes referred to as the theory identified time). $T_s$ represents the moment at which the amplitude of the pulse signal corresponding to the photon begins to be greater than a pre-determined threshold (sometimes referred to as the actual identified moment).

When the actual identified moment is calibrated, the parameters K and b may be obtained by tests in advance. When the parameters K and b are known, a time shift may be obtained. The time shifts corresponding to different rising edge slopes can be different. When the parameters K and b are known, the rising edge slope is a variable and can be obtained in time. When the rising edge slope is obtained, the corresponding time shift is obtained. the theory identified moment is obtained based on the time shift and the actual identified moment.

Figure 4:
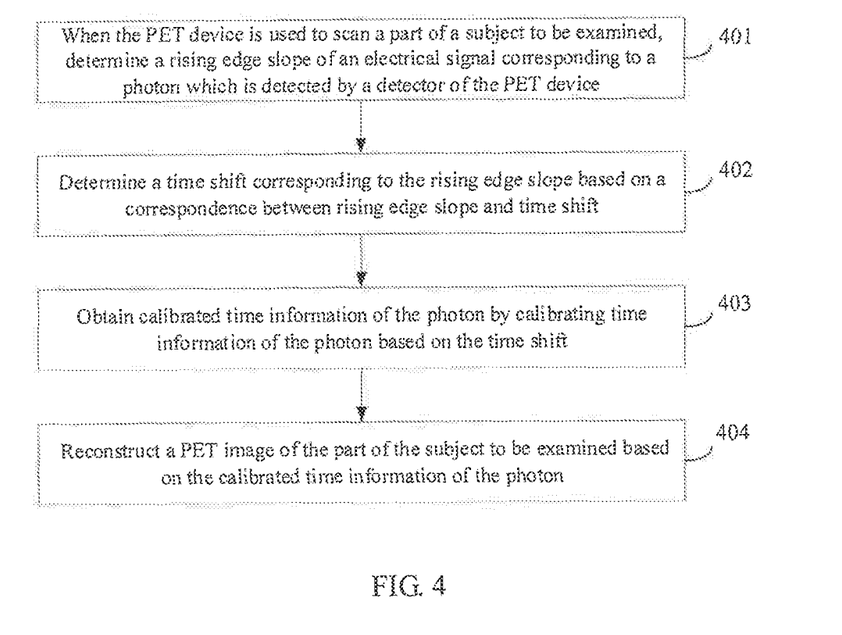
FIG. 4 is a flowchart of a method of calibrating time in a PET device.

FIG. 4 is a schematic flowchart of an example method of calibrating time in a PET device. Taking an electrical signal corresponding to a photon being a voltage signal as an example, the method of calibrating time in the PET device includes elements 401-404.

When the PET device is used to scan a part of a subject to be examined, a rising edge slope of an electrical signal corresponding to a photon which is detected by a detector of the PET device is determined (401).

In an example, determining the rising edge slope includes obtaining a first amplitude at a first moment and a second amplitude at a second moment in a rising edge process of the electrical signal. Determining the rising edge slope also includes determining an amplitude difference between the first amplitude and the second amplitude and a time difference between the first moment and the second moment. The ratio between the amplitude difference and the time difference is taken as the rising edge slope.

In an example, obtaining the first amplitude at the first moment and the second amplitude at the second moment in the rising edge process of the electrical signal includes receiving the electrical signal at respective a first input of a first comparator and a first input of a second comparator. An inverting time of the first comparator is recorded as the first moment and an inverting time of the second comparator is recorded as the second moment. A second input of the first comparator receives a first threshold, the first amplitude being equal to the first threshold. A second input of the second comparator receives a second threshold, the second amplitude being equal to the second threshold. The second threshold is greater than the first threshold.

In an example, obtaining the first amplitude at the first moment and the second amplitude at the second moment in the rising edge process of the electrical signal includes receiving the electrical signal at a first input of a third comparator and an input of an analog-to-digital converter. A second input of the third comparator receives a third threshold. An output of the third comparator is coupled to a control input of the analog-to-digital converter such that an inversion of the third comparator triggers the analog-to-digital converter to perform a sample for an amplitude of the electrical signal. The time difference is equal to a sampling period of the analog-to-digital converter. Two sampling values from successive samplings of the electrical signal by the analog-to-digital converter are obtained as the first amplitude and the second amplitude, respectively.

Figure 5:
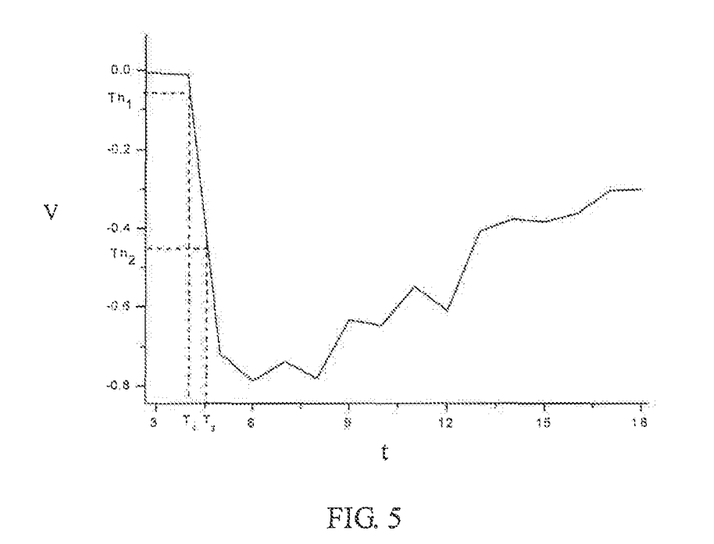
FIG. 5 is a plot of an actual identified moment and a rising edge slope of an electrical signal corresponding to a photon.

Referring to FIG. 5, an amplitude being a voltage is used as an example to demonstrate how to determine a rising edge slope of an electrical signal corresponding to a photon. FIG. 5 is a schematic diagram of an example of an actual identified moment and a rising edge slope of an electrical signal corresponding to a photon. The pulse signal corresponding to the photon is a negative pulse signal and in the in the context of this disclosure, a falling edge slope obtained from FIG. 5 is referred to as the rising edge slope.

The horizontal axis represents an actual identified moment determined based on the electrical signal corresponding to the photon and the vertical axis represents a voltage of the electrical signal corresponding to the photon. The rising edge slope of the electrical signal corresponding to the photon can be obtained by measuring two moments at which a voltage of the electrical signal corresponding to the photon, e.g., in the rising edge, reaches at least two pre-determined thresholds.

For example, two actual identified moments $T_1$ and $T_2$ are obtained at corresponding threshold voltages $Th_1$ and $Th_2$. A voltage difference between the threshold voltages $Th_1$ and $Th_2$ is determined and a time difference between the two actual identified moments $T_1$ and $T_2$ is determined. The ratio between the voltage difference and the time difference is taken as the rising edge slope.

Referring again to FIG. 4, a time shift corresponding to the rising edge slope is determined based on a correspondence between rising edge slope and the time shift (402). In some examples, there is a linear relationship between the time shift and the rising edge slope, and the time shift corresponding to the rising edge slope can be determined according to the linear relationship. The linear relationship may be pre-stored before the PET device begins to scan the subject, e.g., having been determined in a pre-scanning calibration process.

Time information of the photon is is calibrated based on the time shift (403) and a PET image of the part of the subject to be examined is reconstructed based on the calibrated time information of the photon (404).

In some examples, an actual identified moment of an electrical signal corresponding to a photon is calibrated based on a correspondence between the time shift and the rising edge slope of the electrical signal corresponding to the photon. First, the rising edge slope is obtained. A corresponding time shift is obtained based on the correspondence between time shift and rising edge slope. Then a theory identified moment is obtained using an actual identified moment and the corresponding time shift. The theory identified moment may represent time information of the photon with a relatively high accuracy. Using this approach, relatively accurate time information can be provided during the subsequent process of reconstructing a PET image, thereby improving the quality of the reconstructed PET image.

The process of obtaining the linear relationship between rising edge slope and time shift of the electrical signal corresponding to the photon is described in detail below. In some examples, this process of obtaining the linear relationship can be performed during the system calibration of the PET device.

The linear relationship between the rising edge slope and the time shift of the electrical signal corresponding to the photon may be expressed as formula (1), reproduced again here for convenience:

$$TimeShift = K*Ri + b \qquad (1).$$

As indicated in formula (1), the linear relationship between rising edge slope and time shift of the electrical signal corresponding to the photon depends on the parameters K and b. In an example, at least two time shifts and at least two rising edge slopes are obtained, and then the parameters K and b in formula (1) are determined according to the time shifts and corresponding rising edge slopes.

In some examples, obtaining the correspondence between rising edge slope and time shift includes determining the rising edge slope of a test electrical signal corresponding to a test photon from a test source detected by the detector of the PET device when the PET device performs a system calibration process. A time shift of the test photon is obtained based on time information of the test photon and time information of a standard photon from a standard source. The correspondence is obtained by fitting based on time shifts and rising edge slopes of at least two test photons.

In an example process of determining the rising edge slope of the test electrical signal, a first amplitude at a first moment and a second amplitude at a second moment in a rising edge process of the test electrical signal are obtained. An amplitude difference between the first amplitude and the second amplitude and a time difference between the first moment and the second moment are determined. A ratio between the amplitude difference and the time difference is taken as the rising edge slope of the test electrical signal.

The following describes an example approach for obtaining the first amplitude at the first moment and the second amplitude at the second moment in the rising edge process of the test electrical signal. This example approach is implemented by two comparators.

Figure 6:
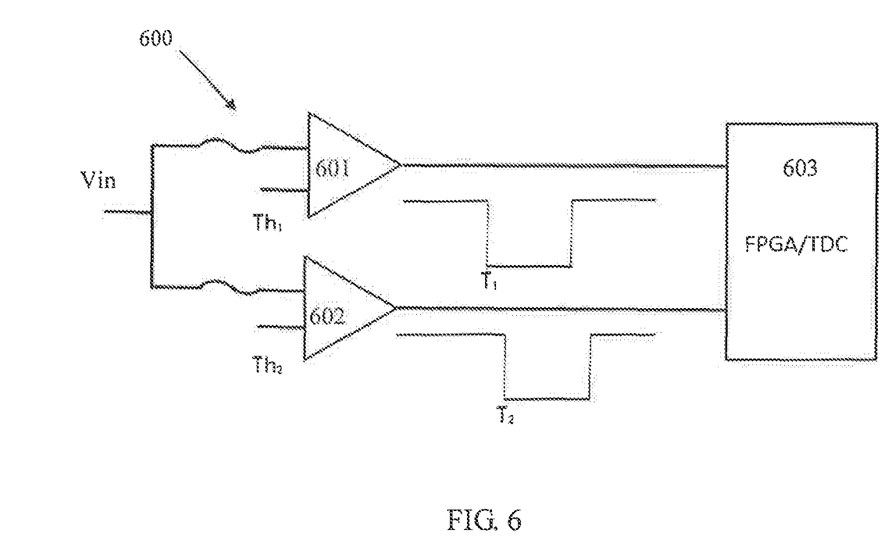
FIG. 6 is a schematic diagram of a circuit structure of an apparatus for obtaining the correspondence.

FIG. 6 is a schematic diagram of an example circuit structure of an apparatus 600 for obtaining the correspondence using two comparators. The apparatus 600 includes a first comparator 601, a second comparator 602, and a computer 603. Generally, the apparatus 600 obtains the rising edge slope of an electrical signal corresponding to a photon based on the difference between the thresholds of the two comparators 601, 602. A first input of the first comparator 601 receives a first threshold $Th_1$ and a second input of the first comparator 601 is coupled to an input Vin of the apparatus to receive the test electrical signal corresponding to the test photon. An output of the first comparator 601 is coupled to a first input of the computer 603. A first input of the second comparator 602 receives a second threshold $Th_2$ and a second input of the second comparator 602 is coupled to the input Vin of the apparatus to receive the test electrical signal corresponding to the test photon. An output of the second comparator 602 is coupled to a second input of the computer 603. The first threshold $Th_1$ is smaller than the second threshold $Th_2$. A relationship between the first threshold $Th_1$ and the second threshold $Th_2$ can be expressed as the following formula (3):

$$|Th_1| < |Th_2| \qquad (3).$$

When the test electrical signal corresponding to the test photon is input to the input Vin of the apparatus, obtaining the rising edge slope of the test electrical signal corresponding to the test photon with the apparatus includes obtaining a inverting time $T_{1-1}$ of the first comparator 601 and obtaining a inverting time $T_{2-1}$ of the second comparator 602. The rising edge slope of the test electrical signal corresponding to the test photon can then be obtained by the following formula (4):

$$Ri = |(Th_2 - Th_1)/(T_{2-1} - T_{1-1})| \qquad (4).$$

i represents a serial number of the test electrical signal corresponding to the test photon. With the apparatus shown in FIG. 6, a rising edge slope can be obtained based on a difference between the threshold voltages of the two comparators and a difference between the inverting times of the two comparators.

In some examples, the first threshold $Th_1$ may be between about 15% and about 25% of the amplitude of the electrical signal corresponding to the photon, e.g., about 15%, about 20%, or about 25%. The second threshold $Th_2$ may be between about 30% and about 40% of the amplitude of the electrical signal corresponding to the photon, e.g., about 30%, about 35%, or about 40%. However, specific ranges of the first threshold $Th_1$ and the second threshold $Th_2$ are not limited in the present disclosure and depend on a desired calibration effect. The first threshold $Th_1$ can be used as the first amplitude and the second threshold $Th_2$ can be used as the second amplitude.

In some examples, the test photon can be a gamma photon emitted by the test source during the system calibration of the PET device and an electrical signal corresponding to the test photon is referred to as a test electrical signal. To increase the accuracy of the parameters K and b determined based on the test photons, the selected test photons can include multiple types of photons that may be detected during the actual operation of the detector, e.g., as many types of photons as is feasible.

In an example, the computer 603 includes a Field-Programmable Gate Array (FPGA) or a Time-to-Digital Converter (TDC). The computer 603 first obtains the inverting time of the first comparator 601 and the inverting time of the second comparator 602 when the test electrical signal corresponding to the test photon is input to the input Vin of the apparatus, and then obtains the rising edge slope of the test electrical signal corresponding to the test photon with the above formula (4) based on the known first threshold $Th_1$ and second threshold $Th_2$.

The apparatus shown in FIG. 6 can be applied to electrical signals corresponding to multiple photons. The serial number of a given electrical signal is represented by I, where i is an integer no less than 1. For example, i=1 represents a first electrical signal corresponding to a first photon, i=2 represents a second electrical signal corresponding to a second photon, and so on. The apparatus can determine two actual identified moments for the electrical signal corresponding to the respective photons.

Since the second threshold is greater than the first threshold, i.e., $|Th_1| > |Th_2|$, for an electrical signal corresponding to a photon, the first comparator 601 is first inverted and then the second comparator 602 is inverted. For example, it can be seen from the schematic diagram of the valid output signals of the comparators 601 and 602 in FIG. 6 that a low level start moment $T_1$ of an output signal of the first comparator 601 is ahead of a low level start moment $T_2$ of an output signal of the second comparator 602.

Based on an actual identified moment of the test electrical signal corresponding to the test photon and a theory identified moment of the test electrical signal corresponding to the test photon which is obtained from the standard source (e.g., a gamma photon source capable of emitting a gamma photon having a fixed energy of 511 keV), a time shift of the test electrical signal corresponding to the test photon can be obtained according to formula (2):

$$\text{TimeShift} = T_Z - T_S \tag{2}$$

where $T_Z$ represents the theory identified moment of the test electrical signal corresponding to the test photon and $T_S$ represents the actual identified moment of the test electrical signal corresponding to the test photon. When the rising edge slope of the test electrical signal is obtained by the apparatus shown in FIG. 6, the inverting time of the first comparator 601 is taken as the actual identified moment of the test electrical signal.

When there is a linear relationship between time shift and rising edge slope, the parameters K and b in the linear relationship can be obtained by fitting based on time shifts and rising edge slopes of test electrical signals corresponding to at least two test photons. The process of obtaining two parameters K and b is a process of obtaining two unknowns in a binary equation. The parameters K and b can be obtained by fitting based on time shifts and rising edge slopes of at least two test photons. In an actual situation, the probability that the rising edge slope of the electrical signal corresponding to two distinct photons is same is extremely small. This allows the parameters K and b to be obtained based on time shifts and rising edge slopes of test electrical signals corresponding to at least two test photons. For instance, based on time shifts and rising edge slopes of test electrical signals corresponding to at least two test photons, the parameters K and b can be obtained by fitting, for example, linear fitting or other suitable fitting types. In an example, the parameters K and b are obtained by fitting with a Matlab calculation tool.

An actual identified moment of an electrical signal corresponding to a photon may be measured by the apparatus shown in FIG. 6. An inverting time of the first comparator 601 is a first actual identified moment (sometimes referred to as a first moment) of the electrical signal corresponding to the photon. An inverting time of the second comparator 602 is a second actual identified moment (sometimes referred to as a second moment) of the electrical signal corresponding to the photon. The two actual identified moments of the electrical signal corresponding to the photon may be obtained by detecting the inverting time of the first comparator 601 and the second comparator 602.

A theory identified moment of the test electrical signal corresponding to the test photon is obtained by the standard source. For instance, the standard source can be a gamma photon source capable of emitting a gamma photon having an energy of 511 keV. In some examples, information about the test photon is obtained during the system calibration of the PET device. For instance, during the system calibration of the PET device, the standard source may emit a gamma photon. Information of the gamma photon is the same as that of the test photon, except for the photon energy. The first comparator 601 receives an electrical signal corresponding to the gamma photon and under the first threshold $Th_1$, an inverting time of the first comparator 601 may be taken as the theory identified moment of the test electrical signal corresponding to the test photon.

When a theory identified moment $T_Z$ and an actual identified moment $T_S$ of a test electrical signal corresponding to a test photon are obtained, a time shift of the test electrical signal corresponding to the test photon can be obtained according to formula (2).

Since the second threshold $Th_2$ is greater than the first threshold $Th_1$, in some situations, the computer 603 may receive a valid output signal of the first comparator 601 without receiving a valid output signal of the second comparator 602. The computer 603 may interpret these situations as representing invalid signals. For instance, the computer 603 may be configured to process only cases in which the output signals of the first comparator 601 and the second comparator 602 both are valid signals.

Figure 7:
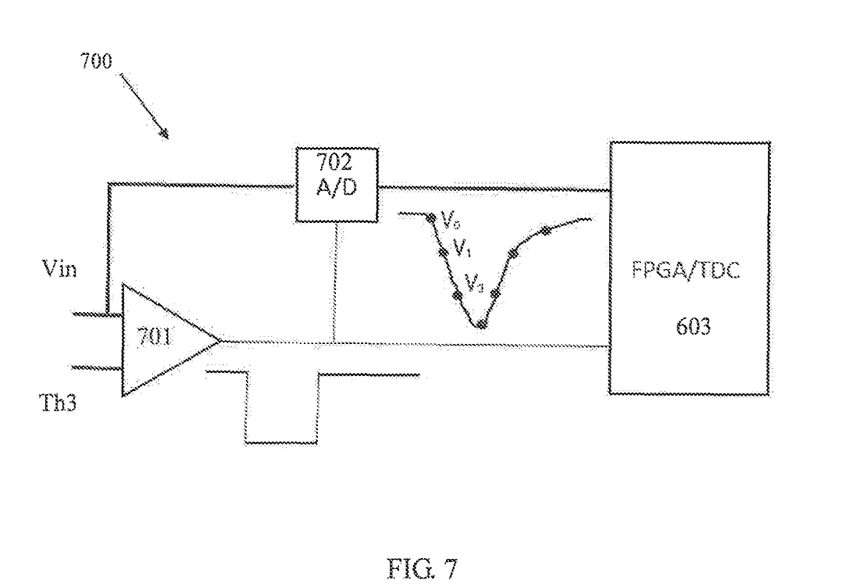
FIG. 7 is a schematic diagram of a circuit structure of an apparatus for obtaining the correspondence.

The following describes an example approach for obtaining the first amplitude at the first moment and the second amplitude at the second moment in the rising edge process of the test electrical signal. This example approach is implemented by a comparator and an analog-to-digital converter (ADC). FIG. 7 is a schematic diagram of an example circuit structure of an apparatus 700 for obtaining the correspondence using a comparator and an ADC. The apparatus 700 includes a third comparator 701, an ADC 702 and a computer 703. In some examples, the computer 703 can be the computer 603 of FIG. 6. Generally, the apparatus 700 obtains the amplitude difference using the ADC 702 and the third comparator 701. A first input of the third comparator 701 is coupled to an input Vin of the apparatus to receive the test electrical signal corresponding to the test photon, and a second input of the third comparator 701 receives a third threshold $Th_3$. An output of the third comparator 701 is coupled to a control input of the ADC 702 and a first input of the computer 603. An analog signal input of the ADC 702 is coupled to the input Vin of the apparatus to receive the test electrical signal corresponding to the test photon; and an output of the ADC 702 is coupled to a second input of the computer 603.

When the test electrical signal corresponding to the test photon is input to the input Vin of the apparatus, obtaining the rising edge slope of the test electrical signal corresponding to the test photon with the apparatus includes obtaining an inverting time $T_i$ of the third comparator 701, where an inversion of the third comparator 701 triggers the ADC 702 to perform a sample for an amplitude of the test electrical signal corresponding to the test photon. The rising edge slope of the test electrical signal corresponding to the test photon is obtained by formula (5-1) or formula (5-2):

$$Ri = |(V_1 - V_2)/T| \tag{5-1; and}$$

$$Ri = |\Sigma_{i=1}^{n}(V_i - V_{i+1})/nT| \tag{5-2}$$

$V_1$ and $V_2$ represent amplitudes, such as voltages, of the test electrical signal corresponding to the test photon collected by the ADC 702 in adjacent first and second sampling periods. $V_i$ and $V_{i+1}$ represent amplitudes, such as voltages, of the test electrical signal corresponding to the test photon collected by the ADC 702 in adjacent sampling periods. n represents a number of sampling periods. T represents a sampling period of the ADC 702. It can be seen from formula (5-1) that two sampling values obtained by the ADC 702 from successive samplings of the test electrical signal are determined as the first amplitude and the second amplitude respectively.

The ADC 702 samples an amplitude of an electrical signal corresponding to a photon according to the sampling period. A difference between amplitudes of an electrical signal corresponding to a photon in two adjacent sampling periods is divided by the sampling period to obtain a rising edge slope, e.g., according to formula (5-1).

In some examples, to improve the accuracy of the rising edge slope, the rising edge slope is obtained by averaging of multiple sampling values over the total duration of the corresponding sampling periods of the ADC 702. For example, a number n of amplitude differences is obtained, and the sum of the n amplitude differences is divided by the sum of n sampling periods to obtain the rising edge slope, e.g., according to formula (5-2). n is an integer, e.g., an integer no less than 3.

In some examples, the computer 603 continues to obtain a sampling value output by the ADC 702 after obtaining an inverting time of the third comparator 701. The third comparator 701 is inverted when an amplitude of an electrical signal corresponding to a photon begins to be greater than a threshold. The rising edge slope is obtained with the formula (5-1) or the formula (5-2).

Further processing proceeds according to the description provided above for the example of FIG. 6.

The parameters K and b in the linear relationship may be stored, e.g., in the FPGA or TDC. When calibrating time information of a photon, the FPGA or TDC can be accessed to carry out calculation.

When the ADC 702 is used to obtain a rising edge slope, a sampling rate of the ADC 702 can be set such that there are at least two sampling points in the rising edge. The ADC 702 is not only used to obtain a rising edge slope of an electrical signal corresponding to a photon, but also to obtain energy information of the photon. Given that an ADC is typically a component of a PET detector, the apparatus 700 of FIG. 7 does not cause a significant increase design complexity of the PET system.

In the above examples, in addition to the use of a comparator, a digital threshold comparison format can be used. For example, a full digital pulse waveform can be obtained, and time information of a photon can be calibrated by taking a numerical value as a threshold for comparison.

When time information of a photon is calibrated, a theory identified moment is obtained by FPGA and TDC, or associated data is transmitted to an upper computer and then the actual identified moment is obtained by the upper computer. The calculation can be a direct calculation or a lookup in a table.

Figure 8:
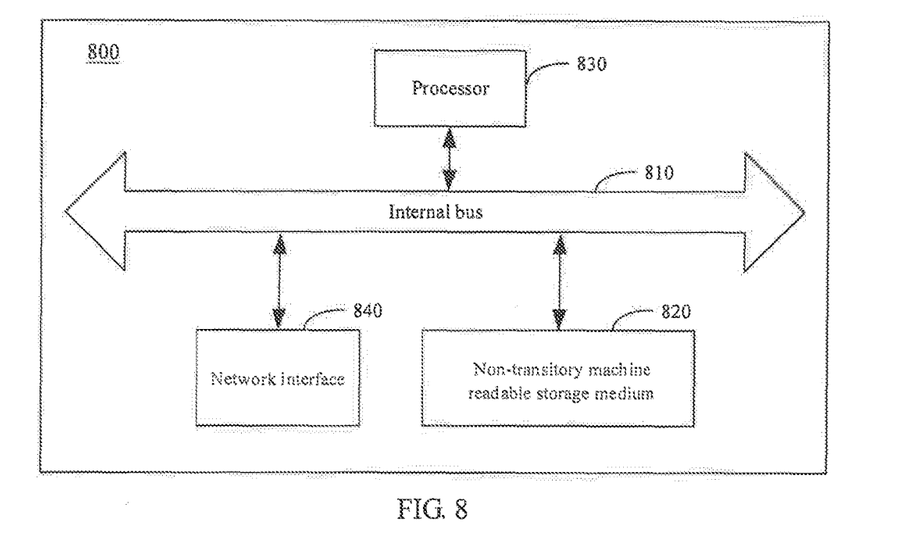
FIG. 8 is a schematic diagram of a partial hardware structure of a PET device.

FIG. 8 is a schematic diagram of a partial hardware structure of an example PET device 800 with capability for calibrating time, e.g., using one or more of the approaches described above. The PET device includes an internal bus 810, an non-transitory machine readable storage medium 820, a processor 830, a network interface 840, and a detector (not shown in FIG. 8) coupled with the network interface 840. The processor 830 may invoke machine executable instructions stored in the non-transitory machine readable storage medium 820 to calibrate time in the PET device. In some examples, the processor 830 includes a TDC and a FPGA.

Some aspects of the approaches for calibrating time involves hardware, such as a comparator, an ADC, or other hardware. This hardware can also be incorporated in the PET device 800.

the comparators in the above examples are not limited to a certain kind of comparator chip, and may include different types of comparator chips. In some examples, the function of the comparator can be implemented in another device capable of carrying out the comparator function. For example, a low voltage differential signals (LVDS) interface of an FPGA may be applied to implement the comparator function.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description provides examples and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications fall within the protection scope of the technical scheme of the present disclosure. Accordingly, other embodiments are within the scope of the following claims.

What is claimed is:

1. A method of calibrating time in a Positron Emission Computed Tomography (PET) device, the method comprising:
    determining a rising edge slope of an electrical signal corresponding to a photon which is detected by a detector of the PET device when the PET device is used to scan a part of a subject to be examined;
    determining a time shift corresponding to the rising edge slope based on a correspondence between the rising edge slope and the time shift;
    calibrating time information of the photon based on the time shift; and
    reconstructing a PET image of the part of the subject to be examined based on the calibrated time information of the photon.

2. The method of claim 1, wherein determining the rising edge slope of the electrical signal comprises:
    obtaining a first amplitude at a first moment and a second amplitude at a second moment in a rising edge process of the electrical signal;
    determining an amplitude difference between the first amplitude and the second amplitude;
    determining a time difference between the first moment and the second moment; and
    determining a ratio between the amplitude difference and the time difference, the ratio being taken as the rising edge slope.

3. The method of claim 2, wherein obtaining the first amplitude at the first moment and the second amplitude at the second moment in the rising edge process of the electrical signal comprises:
    receiving the electrical signal at a first input of a first comparator and a first input of a second comparator;
    receiving a first threshold at a second input of the first comparator, the first amplitude being equal to the first threshold;
    receiving a second threshold at a second input of the second comparator, the second amplitude being equal to the second threshold, and the second threshold being greater than the first threshold;
    recording an inverting time of the first comparator as the first moment; and recording an inverting time of the second comparator as the second moment.

4. The method of claim 2, wherein obtaining the first amplitude at the first moment and the second amplitude at the second moment in the rising edge process of the electrical signal comprises:
receiving the electrical signal at a first input of a third comparator and an input of an analog-to-digital converter;
receiving a third threshold at a second input of the third comparator,
wherein an output of the third comparator is coupled to a control input of the analog-to-digital converter such that an inversion of the third comparator triggers the analog-to-digital converter to perform a sample for an amplitude of the electrical signal, and wherein the time difference is equal to a sampling period of the analog-to-digital converter; and
obtaining two sampling values from successive samplings of the electrical signal by the analog-to-digital converter, the two sampling values being the first and second amplitudes.

5. The method of claim 1, comprising:
obtaining the correspondence between the rising edge slope and the time shift for the PET device prior to the PET device being used to scan the part of the subject to be examined.

6. The method of claim 5, wherein obtaining the correspondence between rising edge slope and time shift comprises:
determining a rising edge slope of a test electrical signal corresponding to a test photon from a test source detected by the detector of the PET device when the PET device performs a system calibration process;
obtaining a time shift of the test photon based on time information of the test photon and time information of a standard photon from a standard source; and
obtaining the correspondence by fitting based on time shifts and rising edge slopes of test electrical signals corresponding to at least two test photons.

7. The method of claim 6, wherein determining the rising edge slope of the test electrical signal comprises:
obtaining a first amplitude at a first moment and a second amplitude at a second moment in a rising edge process of the test electrical signal;
determining an amplitude difference between the first amplitude and the second amplitude;
determining a time difference between the first moment and the second moment; and
determining a ratio between the amplitude difference and the time difference, the ratio being taken as the rising edge slope.

8. The method of claim 7, wherein obtaining the first amplitude at the first moment and the second amplitude at the second moment in the rising edge process of the test electrical signal comprises:
receiving the test electrical signal at a first input of a first comparator and a first input of a second comparator;
receiving a first threshold at a second input of the first comparator, the first amplitude being equal to the first threshold,
receiving a second threshold at a second input of the second comparator, the second amplitude being equal to the second threshold, the second threshold being greater than the first threshold;
recording an inverting time of the first comparator as the first moment; and
recording an inverting time of the second comparator as the second moment.

9. The method of claim 7, wherein obtaining the first amplitude at the first moment and the second amplitude at the second moment in the rising edge process of the test electrical signal comprises:
receiving the test electrical signal at a first input of a third comparator and an input of an analog-to-digital converter;
receiving a third threshold at a second input of the third comparator,
wherein an output of the third comparator is coupled to a control input of the analog-to-digital converter such that an inversion of the third comparator triggers the analog-to-digital converter to perform a sample for an amplitude of the test electrical signal;
wherein the time difference is equal to a sampling period of the analog-to-digital converter;
obtaining two sampling values from successive sampling of the test electrical signal by the analog-to-digital converter, the two sampling values being the first and second amplitudes.

10. The method of claim 6, wherein determining the rising edge slope of the test electrical signal comprises:
receiving the test electrical signal at a first input of a third comparator and an input of an analog-to-digital converter;
receiving a third threshold at a second input of the third comparator,
wherein an output of the third comparator is coupled to a control input of the analog-to-digital converter such that a inversion of the third comparator triggers the analog-to-digital converter to perform a sample for an amplitude of the test electrical signal;
obtaining at least three sampling values from successive sampling of the test electrical signal by the analog-to-digital converter; and
determining the rising edge slope of the test electrical signal based on the at least three sampling values and the sampling period of the analog-to-digital converter.

11. A PET device, comprising:
a detector; and
one or more processors; and
a non-transitory machine readable storage medium;
wherein the one or more processors are configured to invoke machine executable instructions stored on the non-transitory machine readable storage medium to:
determine a rising edge slope of an electrical signal corresponding to a photon which is detected by the detector when the PET device is used to scan a part of a subject to be examined;
determine a time shift corresponding to the rising edge slope based on a correspondence between the rising edge slope and the time shift;
calibrating time information of the photon based on the time shift; and
reconstruct a PET image of the part of the subject to be examined based on the calibrated time information of the photon.

12. The device according to claim 11, wherein determining the rising edge slope of the electrical signal comprises:
obtaining a first amplitude at a first moment and a second amplitude at a second moment in a rising edge process of the electrical signal;
determining an amplitude difference between the first amplitude and the second amplitude;

determining a time difference between the first moment and the second moment; and determining a ratio between the amplitude difference and the time difference, the ratio being taken as the rising edge slope.

13. The device of claim 12, comprising a first comparator and a second comparator;

wherein obtaining the first amplitude at the first moment and the second amplitude at the second moment in the rising edge process of the electrical signal comprises:

receiving the electrical signal at a first input of the first comparator and a first input of the second comparator;

receiving a first threshold at a second input of the first comparator, the first amplitude being equal to the first threshold, receiving a second threshold at a second input of the second comparator, the second amplitude being equal to the second threshold, and the second threshold being greater than the first threshold;

recording an inverting time of the first comparator as the first moment; and recording an inverting time of the second comparator as the second moment.

14. The device of claim 12, comprising a third comparator and an analog-to-digital converter;

wherein obtaining the first amplitude at the first moment and the second amplitude at the second moment in the rising edge process of the electrical signal comprises:

receiving the electrical signal at a first input of the third comparator and an input of the analog-to-digital converter;

receiving a third threshold at a second input of the third comparator, wherein an output of the third comparator is coupled to a control input of the analog-to-digital converter such that an inversion of the third comparator triggers the analog-to-digital converter to perform a sample for an amplitude of the electrical signal, and wherein the time difference is equal to a sampling period of the analog-to-digital converter; and obtaining two sampling values from successive samplings of the electrical signal by the analog-to-digital converter, the two sampling values being the first and second amplitudes.

15. The device of claim 12, wherein the one or more processors are configured to invoke the machine executable instructions to:

obtain the correspondence between the rising edge slope and the time shift for the PET device prior to the PET device being used to scan the part of the subject to be examined.

16. The device of claim 15, wherein obtaining the correspondence between rising edge slope and time shift comprises:

determining a rising edge slope of a test electrical signal corresponding to a test photon from a test source detected by the detector of the PET device when the PET device performs a system calibration process;

obtaining a time shift of the test photon based on time information of the test photon and time information of a standard photon from a standard source; and obtaining the correspondence by fitting based on time shifts and rising edge slopes of test electrical signals corresponding to at least two test photons.

17. The device of claim 16, wherein determining the rising edge slope of the test electrical signal comprises:

obtaining a first amplitude at a first moment and a second amplitude at a second moment in a rising edge process of the test electrical signal;

determining an amplitude difference between the first amplitude and the second amplitude;

determining a time difference between the first moment and the second moment; and determining a ratio between the amplitude difference and the time difference, the ratio being taken as the rising edge slope.

18. The device of claim 17, comprising a first comparator and a second comparator;

wherein obtaining the first amplitude at the first moment and the second amplitude at the second moment in the rising edge process of the test electrical signal comprises:

receiving the test electrical signal at a first input of the first comparator and a first input of the second comparator;

receiving a first threshold at a second input of the first comparator, the first amplitude being equal to the first threshold, receiving a second threshold at a second input of the second comparator, the second amplitude being equal to the second threshold, and the second threshold being greater than the first threshold;

recording an inverting time of the first comparator as the first moment; and recording an inverting time of the second comparator as the second moment.

19. The device of claim 17, comprising a third comparator and an analog-to-digital converter;

wherein obtaining the first amplitude at the first moment and the second amplitude at the second moment in the rising edge process of the test electrical signal comprises:

receiving the test electrical signal at a first input of the third comparator and an input of the analog-to-digital converter;

receiving a third threshold at a second input of the third comparator, wherein an output of the third comparator is coupled to a control input of the analog-to-digital converter such that an inversion of the third comparator triggers the analog-to-digital converter to perform a sample for an amplitude of the test electrical signal, and wherein the time difference is equal to a sampling period of the analog-to-digital converter; and obtaining two sampling values from successive samplings of the test electrical signal by the analog-to-digital converter, the two sampling values being the first and second amplitudes.

20. The device of claim 11, wherein the processor comprises one or more of a Field-Programmable Gate Array (FPGA) or a Time-to-Digital Converter (TDC).

* * * * *